US008546460B2

(12) United States Patent
Brunner et al.

(10) Patent No.: US 8,546,460 B2
(45) Date of Patent: Oct. 1, 2013

(54) ULTRA HIGH MOLECULAR WEIGHT POLYETHYLENE FOR BEARING SURFACES

(75) Inventors: Lorenz Brunner, Zurich (CH); Yvo Dirix, Erlenbach (CH); Hans Schmotzer, Birmensdorf (CH); Shilesh C. Jani, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 299 days.

(21) Appl. No.: 12/673,266

(22) PCT Filed: Sep. 4, 2008

(86) PCT No.: PCT/US2008/075232
§ 371 (c)(1),
(2), (4) Date: Feb. 12, 2010

(87) PCT Pub. No.: WO2009/032909
PCT Pub. Date: Mar. 12, 2009

(65) Prior Publication Data
US 2011/0112646 A1 May 12, 2011

Related U.S. Application Data

(60) Provisional application No. 60/969,870, filed on Sep. 4, 2007.

(51) Int. Cl.
C08F 2/42 (2006.01)
C08F 2/48 (2006.01)
C08J 3/28 (2006.01)
A61F 2/02 (2006.01)

(52) U.S. Cl.
USPC ........... 522/161; 522/75; 264/494; 623/11.11

(58) Field of Classification Search
USPC ................. 522/75, 161; 264/494; 526/352, 526/351; 524/1, 110, 585, 587; 623/11.11; 523/113, 115, 123
See application file for complete search history.

(56) References Cited

U.S. PATENT DOCUMENTS

| | | | |
|---|---|---|---|
| 5,414,049 A | 5/1995 | Sun et al. | |
| 5,879,400 A | 3/1999 | Merrill et al. | |
| 6,228,900 B1 | 5/2001 | Shen et al. | |
| 6,277,390 B1 | 8/2001 | Schaffner | |
| 6,448,315 B1 | 9/2002 | Lidgren et al. | |
| 6,641,617 B1 * | 11/2003 | Merrill et al. | 623/23.58 |
| 6,852,773 B2 * | 2/2005 | Tanabe et al. | 522/171 |
| 7,846,376 B2 * | 12/2010 | Abt et al. | 264/494 |
| 2007/0059334 A1 * | 3/2007 | Abt et al. | 424/423 |

FOREIGN PATENT DOCUMENTS

| | | |
|---|---|---|
| CA | 256129 A | 12/1925 |
| CZ | 221404 A | 4/1983 |
| EP | 0722973 A1 | 7/1996 |
| JP | 11239611 A | 9/1999 |
| JP | 2009-504283 A | 2/2009 |
| JP | 2009-504897 A | 2/2009 |
| JP | 2010-523805 A | 7/2010 |
| JP | 2010-529213 A | 8/2010 |
| WO | 01/80778 A1 | 11/2001 |
| WO | 2004064618 A2 | 8/2004 |
| WO | 2005/074619 A2 | 8/2005 |
| WO | 2005110276 A1 | 11/2005 |
| WO | 2007019874 A1 | 2/2007 |
| WO | WO 2007/019874 | 2/2007 |
| WO | WO 2007/024684 | 3/2007 |
| WO | WO 2008/109515 | 9/2008 |
| WO | WO 2008/124825 | 10/2008 |

OTHER PUBLICATIONS

European Patent Office examination of the Application No. 08 799 161.8-1219, dated Dec. 23, 2010 (6 pages).
Parth M et al: "Studies on the effect of electron beam radiation on the molecular structure of ultra-high molecular weight polyethylene under the influence of alpha-tocopherol with respect to its application in medical implants", Journal of Materals Science. Materials in Medicine, Chapman and Hall, London, GB.
Willert H.G., Bertram G.H., Clin Orthop 258, 95, 1990.
Costa L., Jacobson K., Bracco P., Brach del Prever E.M., Biomaterials 23, 1613, 2002.
Kurtz S.M., Hozack W., Marcolongo M., Turner J., Rimnac C., Edidin A., J Arthroplasty 18, 68-78, 2003.
Oonishi H., Kadoya Y., Masuda S., Journal of Biomedical Materials Research, 58, 167, 2001.
Grobbelaar C.J., du Plessis T.A., Marais F., The Journal of Bone and Joint Surgery, 60-B, 370, 1978.
Lewis G., Biomaterials, 22, 371, 2001.
McKellop H. et al., J. Orth. Res., 17, 157, 1999.
Collier J.P. et al., Clinical Orthopaedics and Related Research, 414, 289-304, 2003.
Muratoglu O.K. et al., Biomaterials, 20, 1463-1470, 1999.
Wannomae K.K., Bhattacharyya S., Freiberg A., Estok D., Harris W.H., Muratoglu O.J., Arthroplasty, 21, 1005, 2006.
Ries M.D., Pruitt L., Clinical Orthopaedics and Related Research, 440, 149, 2005.

(Continued)

Primary Examiner — Sanza McClendon
(74) Attorney, Agent, or Firm — Krieg DeVault LLP

(57) ABSTRACT

A prosthetic device may comprise an insert having a first surface configured to contact a first prosthetic component and a bearing surface configured to articulate against a second prosthetic component. The insert comprises an ultra-high molecular weight polyethylene and vitamin E. The vitamin E may have a concentration in the range of 0.02 to 0.12 wt % first mixed with the ultra-high molecular weight polyethylene and then molded with the ultra-high molecular weight polyethylene at a temperature greater than the melting point of the ultra-high molecular weight polyethylene. The ultra-high molecular weight polyethylene and vitamin E may be gamma irradiated with a dosage of radiation between 5 and 20 Mrad. The insert may be machined prior to gamma irradiating the insert in air such that the gamma irradiation, at suitably high dosages, may also sterilize the insert.

23 Claims, 3 Drawing Sheets

(56) References Cited

OTHER PUBLICATIONS

Oral E. et al., Biomaterials, 26, 6657, 2005.
Kurtz S. Mazzucco D.C., Siskey R.L., Dumbleton J., Manley M., Wang A., Trans. ORS 2007, 0020.
First Office Action; Chinese Patent Office; Chinese Patent Application 200880114162.0; Jul. 16, 2012, 21 pages.
M. Parth et al., Studies on the effect of electron beam radiation on the molecular structure of ultra-high molecular weight polyethylene under the influence of a-tocopherol with respect to its application in medical implants, Journal of Materials Science: Materials in Medicine, 2002, pp. 917-921, vol. 13 Issue 10, Copyright 2002 Kluwer Academic Publishers.
First Office Action; Japanese Patent Office; Japanese Patent Application 2010-524135; Jun. 4, 2013; 7 pages.

* cited by examiner

Figure 1

Table 3: Expansion of Tables 1 and 2 by the material of the present invention.

| Radiation dose | Free radical content | Wear resistance ($\sim M_c$) | Mechanical properties | Oxidation resistance |
|---|---|---|---|---|
| 0 Mrad | 0 | 0 | 0 | 0 |
| ✓ (e.g. 3 Mrad) | ↑ | + | - | - |
| ✓✓ (e.g. 7 Mrad) | ↑↑ | ++ | -- | -- |
| ✓✓✓ (e.g. 14 Mrad) | ↑↑↑ | +++ | --- | --- |
| ✓✓✓ remelted | 0 | +++ | --- | 0 |
| ✓✓✓ annealed | ↑ | +++ | -- | -- |
| ✓✓✓ high vitE content | 0 | + | -- | 0 |
| Present Material | ↑↑ | +++ | - | 0 |

Figure 2

| | Yield Stress [MPa] | Tensile Strength [MPa] | Elongation at Break [%] | Charpy Impact [kJ/m²] |
|---|---|---|---|---|
| PE gamma-sterilized | 25.8±1.1 | 49.6±6.5 | 414.0±42.0 | 152.2±6.9 |
| PE 7 Mrad remelted | 22.6±0.6 | 32.2±3.6 | 351.3±25.9 | 96.9±1.0 |
| PE 7 Mrad | 23.8±0.6 | 43.7±1.9 | 367.7±15.9 | 108.7±1.1 |
| PE 14 Mrad | 25.8±0.4 | 39.5±9.3 | 241.1±64.6 | 68.8±0.8 |
| 0.1 % VitE 7 Mrad | 24.6±0.2 | 40.9±5.7 | 403.6±50.0 | 144.3±4.4 |
| 0.1 % VitE 7+3 Mrad | 25.5±0.4 | 44.5±3.1 | 388.8±25.9 | 120.4±1.2 |
| 0.1 % VitE 14 Mrad | 25.4±0.2 | 43.1±3.5 | 330.7±26.9 | 95.3±4.7 |
| 0.1 % VitE 20 Mrad | 28.7±0.5 | 49.9±3.1 | 279.2±13.4 | |
| 0.05 % VitE 8 Mrad | 26.9±0.4 | 47.1±3.7 | 399.6±33.5 | 119.4±2.3 |
| 0.05 % VitE 8+3 Mrad | 26.9±0.2 | 53.3±5.9 | 394.2±35.1 | 92.0±2.1 |
| 0.05 % VitE 14 Mrad | 27.0±0.4 | 49.8±4.0 | 319.1±27.0 | 77.7±1.7 |
| 0.03 % VitE 10 Mrad | 26.1±0.2 | 50.7±2.1 | 357.8±13.8 | |
| 0.03 % VitE 14 Mrad | 26.8±0.4 | 50.0±2.7 | 308.5±16.0 | |

Figure 3

|  | Free Radical Content [g$^{-1}$] | Max. OI after aging [-] | Bulk OI after aging [-] | M$_c$ [g/mol] |
|---|---|---|---|---|
| PE gamma-sterilized | 1.46E+18 | 0.24 | 0.20 | 6980 |
| PE 7 Mrad | 3.03E+18 | 0.35 | 0.33 | 5430 |
| PE 14 Mrad | 5.87E+18 | 0.55 | 0.50 | 3520 |
| 0.1 % VitE 7 Mrad | 7.92E+17 | 0.07 | < 0.05 | 6000 |
| 0.1 % VitE 7+3 Mrad | 3.11E+18 | 0.09 | 0.05 | 5090 |
| 0.1 % VitE 14 Mrad | 3.87E+18 | 0.11 | < 0.05 | 3980 |
| 0.1 % VitE 20 Mrad | 1.31E+19 | 0.13 | 0.09 | |
| 0.05 % VitE 8 Mrad | 2.57E+18 | 0.12 | < 0.05 | 5820 |
| 0.05 % VitE 8+3 Mrad | 4.11E+18 | 0.09 | < 0.05 | 4380 |
| 0.05 % VitE 14 Mrad | 3.61E+18 | 0.14 | 0.06 | 3790 |
| 0.05 % VitE 20 Mrad | 1.38E+19 | 0.16 | 0.09 | |
| 0.03 % VitE 10 Mrad | 8.33E+18 | 0.09 | 0.06 | |
| 0.03 % VitE 14 Mrad | 1.06E+19 | 0.14 | 0.07 | |

ULTRA HIGH MOLECULAR WEIGHT POLYETHYLENE FOR BEARING SURFACES

CROSS-REFERENCE TO RELATED APPLICATIONS

This application is a National Phase of International Application No. PCT/US2008/075232, filed on Sep. 4, 2008 which claims the benefit of U.S. Provisional Application No. 60/969,870, filed on Sep. 4, 2007. Each prior application is incorporated by reference herein in its entirety.

BACKGROUND OF THE INVENTION

1. Field of the Invention

The invention relates generally to methods for processing ultra-high molecular weight polyethylene for use as a bearing surface. More particularly, the invention relates to methods for processing ultra-high molecular weight polyethylene for use as a bearing surface in artificial joints.

2. Related Art

Ultra-high molecular weight polyethylene (UHMWPE) is the most commonly used bearing material in total joint replacements and was introduced by John Charnley in the early 1960s (The UHMWPE Handbook, edited S. Kurtz, Elsevier, 2004). Since then, a wide variety of applications have been developed in the total joint arthroplasty, as a result of the material's high toughness and good mechanical properties. Although "conventional" UHMWPE has an excellent clinical record, the maximum lifetime of implant systems is restricted due to the wear particles released from the UHMWPE bearing surface (Willert H. G., Bertram H., Buchhorn G. H., Clin Orthop 258, 95, 1990). These wear particles can induce an osteolytic response in the human body leading to local bone resorption and eventually to aseptic loosening of the artificial joint.

A second problem associated with conventional, gamma-sterilized UHMWPE (2.5-4.0 Mrad; S. Kurtz, The UHM-WPE Handbook, Elsevier, 2004), is the oxidative degradation that occurs during shelf ageing. Degradation occurs when the energy of the gamma rays is sufficient to break some of the carbon-carbon or carbon-hydrogen bonds of the polyethylene chains resulting in the formation of free radicals. The amount of free radicals can be measured, for example, by electron spin resonance measurements (ESR).

A standard gamma-sterilized (3 Mrad) UHMWPE implant has a free radical content of 1.46 E+18 g−1 (see free radical content chart in the Examples section below). These radicals partially recombine but some of them are long-living and can react with oxygen present in, or diffusing into, packaging surrounding the implant (Costa L., Jacobson K., Bracco P., Brach del Prever E. M., Biomaterials 23, 1613, 2002). The oxidative degradation reactions lead to embrittlement of the material and therewith reduce the mechanical properties of the material and might lead to fracture of the implant (Kurtz S. M., Hozack W., Marcolongo M., Turner J., Rimnac C., Edidin A., J Arthroplasty 18, 68-78, 2003).

In the 1970s, highly crosslinked UHMWPEs were introduced with the intention of improving the wear resistance of the material (Oonishi H., Kadoya Y., Masuda S., Journal of Biomedical Materials Research, 58, 167, 2001; Grobbelaar C. J., du Plessis T. A., Marais F., The Journal of Bone and Joint Surgery, 60-B, 370, 1978). The UHMWPE materials were gamma irradiated at high doses up to 100 Mrad. In contrast, to gamma sterilize UHMWPE radiation dosages generally range between 2.5 and 4.0 Mrad. The high doses of gamma irradiation on UHMWPE were used to promote the crosslinking process in the material and thereby increase the wear resistance. However, the free radical amount on the polyethylene chains is generally either not reduced or only locally reduced. Therefore these highly crosslinked materials are prone to the same oxidative degradation during shelf ageing or in-vivo use as the gamma-sterilized UHMWPE.

Radiation crosslinking of unstabilized UHMWPE leads to an increase of the number of free radicals and therefore to an undesired, critical oxidation of the material. Additionally, the mechanical properties of highly crosslinked UHMWPE decrease with increasing radiation dose (Lewis G., Biomaterials, 22, 371, 2001). These interactions between radiation dose and properties of unstabilized material that is not subjected to any post-irradiation heat treatment are qualitatively summarized in Table 1.

In Table 1, the benchmark is no radiation (0 Mrad). A "+" in Table 1 shows enhanced performance relative to the benchmark. A "−" in Table 1 shows inferior performance relative to the benchmark. $M_c$, the molecular weight between crosslinks, decreases with increased irradiation dose. Wear resistance was measured during a standard hip simulator test as described by McKellop (McKellop H. et al., J. Orth. Res., 17, 157, 1999). Mechanical properties were measured with a tensile test. Oxidation resistance was measured after artificial ageing according to ASTM F2003.

TABLE 1

Effect of different radiation doses on selected properties of unstabilized UHMWPE that is not subjected to any post-irradiation heat treatment.

| Radiation dose | Free radical content | Wear resistance* ($\sim M_c$) | Mechanical properties** | Oxidation resistance*** |
| --- | --- | --- | --- | --- |
| 0 Mrad | 0 | 0 | 0 | 0 |
| ✦(e.g. 3 Mrad) | ↑ | + | − | − |
| ✦✦(e.g. 7 Mrad) | ↑↑ | ++ | −− | −− |
| ✦✦✦(e.g. 14 Mrad) | ↑↑↑ | +++ | −−− | −−− |

The relations between the radiation dose and the above mentioned properties is also demonstrated by the experiments, results of which are shown in the Examples below. Both free radical content and oxidation index increase with increasing radiation dose; a relation that was already found earlier (Collier J. P. et al., Clinical Orthopaedics and Related Research, 414, 289-304, 2003). The wear resistance, which is related to the molecular weight between crosslinks Mc (Muratoglu O. K. et al., Biomaterials, 20, 1463-1470, 1999), is substantially enhanced by higher radiation doses. Additionally, thermal treatment to reduce or eliminate the number of free radicals has been well known in the art for decades.

These processes can be subdivided into three groups. The first group is irradiation below the melting temperature followed by annealing. The second group is irradiation below the melting temperature followed by remelting. The third group is irradiation in the melt.

Irradiation below the melting temperature followed by annealing below the melting temperature (U.S. Pat. No. 5,414,049, EP0722973). The main disadvantage of this route is the fact that the UHMWPE chains still contain residual free macroradicals which lead to oxidative degradation (Wannomae K. K., Bhattacharyya S., Freiberg A., Estok D., Harris W. H., Muratoglu O. J., Arthroplasty, 21, 1005, 2006).

Irradiation below the melting temperature followed by remelting above the melting temperature (U.S. Pat. No. 6,228,900). The main disadvantage of this processing scheme is that compared with the annealing process, the mechanical properties are reduced by the remelting step (Ries M. D., Pruitt L., Clinical Orthopaedics and Related Research, 440, 149, 2005).

Irradiation in the melt (U.S. Pat. No. 5,879,400, Dijkstra D. J., PhD Thesis, University of Groningen, 1988). The disadvantage of this process is that the crystallinity is substantially reduced and therewith the mechanical performance.

Others have experimented with chemical antioxidants introduced into medical grade UHMWPE to obtain a wear resistant material that combines a good oxidative stability with sufficient mechanical properties. Most of the common antioxidants exhibit reduced or no biocompatibility, and therefore chemical substances already existing in the human body or in nutritional products were sought. In 1982, Dolezel and Adamirova described a procedure to increase the stability of polyolefins for medical implants against biological degradation in living organisms (CZ 221404). They added alpha-, beta-, gamma- or deltatocopherol (vitamin E), or a mixture thereof, to polyethylene resin and subsequently processed the resulting mixtures. However they did not attempt to crosslink the material to improve its wear resistance.

Recently, several groups established different processing procedures and combined the addition of substantial (0.1%-1.8% w/w) amounts of vitamin E with a radiation crosslinking step to improve the wear resistance of the material. Some of these investigators added substantial amounts of vitamin E prior to the consolidation of the UHMWPE powder (JP 11239611, U.S. Pat. No. 6,277,390, U.S. Pat. No. 6,448,315, WO0180778, WO 2005074619) followed by radiation crosslinking. Others diffused the liquid vitamin E into machined products after the irradiation step, occasionally with the aid of elevated temperatures (CA 256129, WO 2004064618, WO 2005110276, WO 2005074619). Addition of substantial amounts of Vitamin E prior to irradiation negatively affects the crosslinking efficiency of the material and limits the improvement of wear resistance (Oral E. et al., Biomaterials, 26, 6657, 2005).

Diffusion of vitamin E into UHMWPE products after irradiation also comprises several drawbacks: due to the diffusion-controlled doping of UHMWPE products, the depth of the vitamin E level remains uncontrolled, inhomogeneous and limited in its spatial dimensions. Although annealing steps after the actual doping process (which is also carried out at elevated temperatures) partially solve the problem of concentration gradients, the final amount of vitamin E in finished products remains unknown.

In addition, some of the above cited procedures are very cumbersome and cost-intensive. U.S. Pat. No. 6,277,390 describes a process using organic solvents, which run the risk of harming the human organism if not removed completely. U.S. Pat. No. 6,448,315 and CA 256129 describe the use of supercritical $CO^2$, an expensive and difficult way to dope the UHMWPE with vitamin E. The diffusion-controlled doping of UHMWPE products described in WO2004064618 and 2005110276 is additionally very time-consuming (up to 48 hour soaking in vitamin E and 24 hour annealing are described).

Both above mentioned methods (post-irradiation heat treatment and the addition of substantial amounts of vitamin E) that were employed to improve the oxidative stability of highly crosslinked UHMWPE aimed towards an elimination of the free radicals.

As was done in Table 1 above, the effect of these two steps on selected properties of UHMWPE parts is shown is Table 2:

TABLE 2

Expansion of Table 1 by two recent advances to increase the oxidation resistance of highly crosslinked UHMWPE.

| Radiation dose | Free radical content | Wear resistance (~$M_c$) | Mechanical properties | Oxidation resistance |
|---|---|---|---|---|
| 0 Mrad | 0 | 0 | 0 | 0 |
| †(e.g. 3 Mrad) | ↑ | + | − | − |
| ††(e.g. 7 Mrad) | ↑↑ | ++ | −− | −− |
| †††(e.g. 14 Mrad) | ↑↑↑ | +++ | −−− | −−− |
| †††remelted | 0 | +++ | −−− | 0 |
| †††annealed | ↑ | +++ | −− | −− |
| †††high vitE content | 0 | + | −− | 0 |

Recently, the addition of trace amounts (<0.05%) of vitamin E prior to sintering was described to protect radiation crosslinked UHMWPE from oxidative degradation (Kurtz S. Mazzucco D. C., Siskey R. L., Dumbleton J., Manley M., Wang A., Trans. ORS 2007, 0020). However, only mechanical testing was conducted within this study and no attention was paid to the wear resistance of the material. According to Kurtz, at a dose of 7.5 Mrad, the highest amounts (0.0375 or 0.05%) of vitamin E have to be applied to retain a high oxidative stability. However, this combination between radiation dose and vitamin E content does not lead to a high wear resistant material. This can easily be concluded by looking at the Mc values of the "0.05% VitE 8 Mrad" sample in Examples below. Mc of this particular sample (5820 g/mol) is in the same order of magnitude as the "0.1% vitE 7 Mrad" (6000 g/mol) which showed only a slight decrease in the wear rate compared to a gamma-sterilized PE (see hip simulator data in Examples below).

Despite all these efforts, the desired combination between high wear resistance, mechanical properties and low oxidation index has not been achieved yet. Thus, there remains a need for an UHMWPE material for use in artificial joint replacements that combines excellent wear resistance, high oxidative stability and superior mechanical properties. These three material properties have not been combined to a satisfying level while maintaining a facile and cost-effective processing procedure.

SUMMARY OF THE INVENTION

It is in view of the above problems that the present invention was developed. The invention is a composition, comprising an ultra-high molecular weight polyethylene and vitamin E. The vitamin E has a concentration in the range of 0.02 to 0.12 wt %. The vitamin E is first mixed with the ultra-high molecular weight polyethylene and then molded with the ultra-high molecular weight polyethylene at a temperature greater than the melting point of the ultra-high molecular weight polyethylene forming a molded composition. The molded composition is gamma irradiated with a dosage of radiation between 5 and 20 Mrad.

In one aspect of the invention, the concentration of vitamin E is in the range of 0.05 to 0.1 wt %.

In another aspect of the invention, the vitamin E is tocopherol.

In yet another aspect, the vitamin E is alpha-tocopherol.

Another aspect provides a composition wherein the gamma irradiation is a dosage within the range of 7 to 13 Mrad, or more particularly within the range of 9 to 11 Mrad.

In another aspect of the invention, the dosage of gamma irradiation is varied proportionally to the concentration of vitamin E.

In yet another aspect, molded composition is gamma irradiated in air or in an inert gas.

Another aspect provides a composition further gamma sterilized with a dosage within the range of 2.5 to 4 Mrad, or more particularly a dosage of 3 Mrad.

In another aspect of the invention, the molded composition undergoes no further thermal treatment.

Another aspect provides the ultra-high molecular weight polyethylene is a powder, the powder having a multimodal molecular weight distribution including a portion of the powder having a low molecular weight.

A method according to an aspect of the invention includes the steps of mixing a vitamin E having a concentration in the range of 0.02 to 0.12 wt % with an ultra-high molecular weight polyethylene. Another step molds the ultra-high molecular weight polyethylene and vitamin E mixture at a temperature greater than the melting temperature of the ultra-high molecular weight polyethylene. Additionally, a step gamma irradiates the molded ultra-high molecular weight polyethylene and vitamin E mixture at a dosage between 5 and 20 Mrad.

In another aspect of the invention, the concentration of vitamin E is in the range of 0.05 to 0.1 wt %.

In yet another aspect, the vitamin E is tocopherol.

Another aspect provides the vitamin E is alpha-tocopherol.

In another aspect of the invention, the irradiating step comprises gamma irradiating the molded ultra-high molecular weight polyethylene and vitamin E mixture at a dosage between 7 and 13 Mrad, or more particularly between 9 and 11 Mrad.

Another aspect of the invention provides varying the concentration of vitamin E proportionally to the dosage of gamma irradiation.

In another aspect of the invention, the gamma irradiating step is performed in air or an inert gas.

In yet another aspect of the invention, the step of gamma sterilizing the gamma irradiated and molded ultra-high molecular weight polyethylene and vitamin E mixture with a dosage between 2.5 and 4 Mrad, and more particularly 3 Mrad.

Another aspect provides that the molded composition undergoes no further thermal treatment.

Another aspect of the invention provides a prosthetic device. The prosthetic device comprises an insert and vitamin E. The insert has a first surface configured to contact a first prosthetic component and a bearing surface configured to articulate against a second prosthetic component. The insert comprises an ultra-high molecular weight polyethylene. The vitamin E has a concentration in the range of 0.02 to 0.12 wt %. The vitamin E is first mixed with the ultra-high molecular weight polyethylene and then molded with the ultra-high molecular weight polyethylene at a temperature greater than the melting point of the ultra-high molecular weight polyethylene. The ultra-high molecular weight polyethylene and vitamin E is gamma irradiated with a dosage of radiation between 5 and 20 Mrad.

Further features, aspects, and advantages of the present invention, as well as the structure and operation of various embodiments of the present invention, are described in detail below with reference to the accompanying drawings.

BRIEF DESCRIPTION OF THE DRAWINGS

The accompanying drawings, which are incorporated in and form a part of the specification, illustrate embodiments of the present invention and together with the description, serve to explain the principles of the invention. In the drawings:

FIG. 1 is a table comparing prior art materials to an embodiment of the material of the invention.

FIG. 2 is a table comparing mechanical properties of gamma irradiated samples versus materials according to embodiments of the invention.

FIG. 3 is a table of crosslinking properties of gamma irradiated samples versus materials according to embodiments of the invention.

DETAILED DESCRIPTION OF THE EMBODIMENTS

Figure 4:
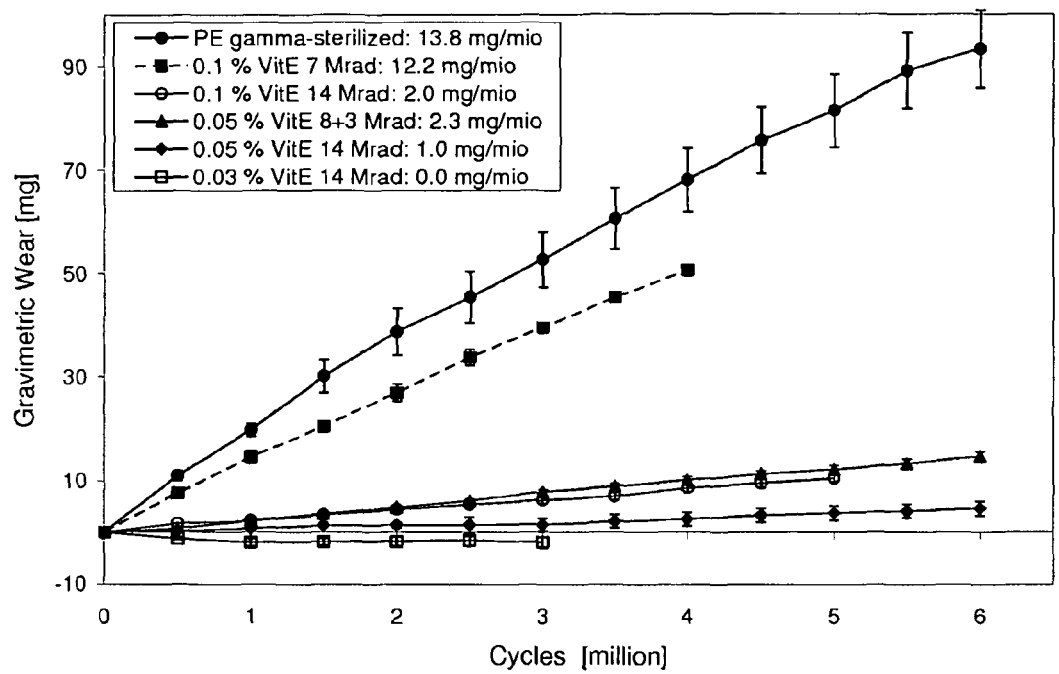
FIG. 4 is a graph of hip simulator data of embodiments of the material relating wear to simulator cycles.

The material of the present invention provides a combination of wear resistance, high oxidative stability and improved mechanical properties for an artificial joint bearing surface. Initially, trace amounts of vitamin E have been added to the UHMWPE powder. As shown in FIG. 1, Table 2 is expanded by the material properties of an embodiment of the present invention. As shown in FIG. 1, this embodiment has decreased free radical content and increased wear resistance while maintaining oxidation resistance while reducing mechanical property losses as compared to gamma irradiated only, annealed, remelted, and high vitamin E content.

Embodiments of the present invention provide an UHMWPE material comprising an easy, facile production process through introduction of vitamin E into UHMWPE powder prior to sintering. The production process is also facilitated by irradiation in air, which minimizes the need for a complicating protective environment.

Embodiments of the present invention provide a UHMWPE where wear resistance is increased by tuning the trace amount of vitamin E to the radiation crosslinking dose.

Addition of vitamin E in trace amounts also sufficiently protects the material from oxidative degradation, as demonstrated by accelerated aging studies. Additionally the trace amounts of vitamin E allow for better mechanical properties as well as allow for no thermal post-irradiation treatment. As well, the free radical content is above gamma-sterilized (3 Mrad) unstabilized UHMWPE material. The method of production of the UHMWPE material is similar to the standard method for producing a preform of UHMWPE. Obtaining the end product from a preform is done by any of the known standard methods, and most typically is accomplished by removing or machining the unwanted parts of the preform to give the final shaped product. This preform can be subjected to a stress-relief annealing process as mentioned in the ISO 5834-2 standard.

The formation of the UHMWPE material according to the present invention begins with mixing trace amounts of vitamin E 0.02-0.12 wt % with the UHMWPE powder. In the examples described hereafter, the UHMWPE powder preferably will be of Ticona GUR® 1020 medical grade UHMWPE. Such powder is well known and can be commercially obtained. Of course, also any other UHMWPE powders can be used (For example Ticona OUR® 1050, DSM UH210, Basell 1900, UHMWPE powders with a high purity). It is preferable that during the mixing process of vitamin E and UHMWPE powder, a fully homogeneous mixture will be obtained. Once vitamin E and UHMWPE powder have been mixed, they are molded into the preform at a temperature which is above the melting point of the UHMWPE powder. Irradiation of the UHMWPE preform by gamma or electron beam radiation will lead to an increase in the crosslink density. An equivalent measure of the density of crosslinks of the material is that of the molecular weight between the crosslinks. Clearly, the higher the crosslink density between the individual UHMWPE polymers, the lower the molecular weight between the crosslinks. Preferably, the irradiation with the gamma or electron beam is at a dose of between 5 and 20 Mrad, which value can be chosen dependent upon the final properties of the UHMWPE material required. Changing the irradiation dose will lead to a difference in the molecular weight between crosslinks and is intended to be chosen on the basis of the desired final product.

The UHMWPE material may include a free radical content (ESR) between 1.5 E+18 g−1 and 5 E+18 g−1. This free radical content may be at least 10% higher than gamma-sterilized UHMWPE (as shown in FIG. 3). The UHMWPE material may include a bulk oxidation index after artificial ageing (at least 2 mm below the surface) of <0.1. For mechanical properties, a yield stress >23 MPa, a tensile strength >40 MPa and an elongation at break >270% may be achieved (as shown in FIG. 2). Material according to the present invention may result in a Charpy impact strength of greater than 30 kJ/m2 (as shown in FIG. 2). A molecular weight between crosslinks (Mc)<4500 g/mol may be achieved (as shown in FIG. 3). The UHMWPE may include a wear rate of <3 mg/mio cycles, as determined on a hip simulator using 28 mm hip cups (as shown in FIG. 4). In the context of traditional material, the wear rate on a hip simulator may be at the most 25% of the wear rate of a conventional, gamma sterilized UHMWPE containing no stabilizer.

Embodiments may vary the amount of vitamin E and the amount of irradiation. The concentration of vitamin E in the preform is preferably 0.02-0.12 wt %, more preferably above 0.05% but below 0.10%. The irradiation dose is preferably 5-20 Mrad, more preferably 7-13 Mrad and even more preferably 9-11 Mrad. Preferably, the small concentrations of vitamin E will be proportionately added with respect to the amount of irradiation dose. Thus, low concentrations of vitamin E within the range of concentrations (such as 0.02 wt %) will be irradiated at low doses of gamma irradiation while high concentrations of vitamin E (such as 0.12 wt %) will be irradiated at high doses of gamma irradiation.

The advantages compared to the prior art may include the unique combination of facile processing, oxidation resistance, wear resistance and mechanical properties of a UHMWPE material that can be used in total joint arthroplasty. This is done by tuning the amount of vitamin E and irradiation dose for the stabilized material. Compared to conventional, gamma-sterilized (3 Mrad) UHMWPE, the material described in the present invention shows higher oxidation resistance (see oxidation chart below) as well as considerably higher wear resistance (see hip simulator graph below). Compared to a material having the same irradiation dose (7 or 14 Mrad) without an additive, the material of the present invention containing vitamin E has no bulk oxidation after artificial ageing (<0.05 versus 0.5, see oxidation chart below). Compared to a material having the same irradiation dose (7 or 14 Mrad) without an additive, the material of the present invention containing vitamin E has superior mechanical properties (see mechanical properties table below). Compared to irradiation crosslinked and subsequently remelted material, the material described in the present invention exhibits superior mechanical properties (yield stress, strength, elongation at fracture and Charpy impact strength), as can be seen in mechanical properties table below.

A composition may comprise an ultra-high molecular weight polyethylene and vitamin E. The vitamin E may have a concentration in the range of 0.02 to 0.12 wt % first mixed with the ultra-high molecular weight polyethylene and then molded with the ultra-high molecular weight polyethylene at a temperature greater than the melting point of the ultra-high molecular weight polyethylene forming a molded composition. The molded composition may be gamma irradiated with a dosage of radiation between 5 and 20 Mrad.

The concentration of vitamin E may more specifically be in the range of 0.05 to 0.1 wt %.

The vitamin E may be tocopherol.

More specifically, the vitamin E may be alpha-tocopherol.

Within the broader range of dosage of gamma irradiation, the gamma irradiation may more specifically be a dosage within the range of 7 to 13 Mrad.

Within the broader range of dosage of gamma irradiation, the gamma irradiation may more specifically be a dosage within the range of 9 to 11 Mrad.

The gamma irradiation may be varied proportionally to the concentration of vitamin E.

Additionally, the molded composition may be gamma irradiated in air.

The composition may further be gamma sterilized with a dosage within the range of 2.5 to 4 Mrad.

More specifically, the composition may be further gamma sterilized with a dosage of 3 Mrad.

The composition may not undergo further thermal treatment.

A method of mixing a composition includes mixing a vitamin E having a concentration in the range of 0.02 to 0.12 wt % with an ultra-high molecular weight polyethylene. Another step molds the ultra-high molecular weight polyethylene and vitamin E mixture at a temperature greater than the melting temperature of the ultra-high molecular weight polyethylene. Another step gamma irradiates the molded ultra-high molecular weight polyethylene and vitamin E mixture at a dosage between 5 and 20 Mrad.

More specifically, the mixing step may include a concentration of vitamin E in the range of 0.05 to 0.1 wt %.

The mixing step may mix vitamin E that is tocopherol.

The mixing step may mix vitamin E that is alpha-tocopherol.

More specifically, the irradiating step may comprise gamma irradiating the molded ultra-high molecular weight polyethylene and vitamin E mixture at a dosage between 7 and 13 Mrad.

More specifically, the irradiating step may comprise gamma irradiating the molded ultra-high molecular weight polyethylene and vitamin E mixture at a dosage between 9 and 11 Mrad.

Additionally, the method may further comprise the step of varying the concentration of vitamin E proportionally to the dosage of gamma irradiation.

The gamma irradiating step may be performed in air.

Additionally, the method may further comprise the step of gamma sterilizing the gamma irradiated and molded ultra-high molecular weight polyethylene and vitamin E mixture with a dosage between 2.5 and 4 Mrad.

The method may further comprise the step of gamma sterilizing the gamma irradiated and molded ultra-high molecular weight polyethylene and vitamin E mixture with a dosage of 3 Mrad.

The method of the molded composition may undergo no further thermal treatment or may include the step of annealing the composition at a temperature less than the melting temperature of the ultra-high molecular weight polyethylene.

A prosthetic device may comprise an insert having a first surface configured to contact a first prosthetic component and a bearing surface configured to articulate against a second prosthetic component. The insert comprises an ultra-high molecular weight polyethylene and vitamin E. The vitamin E may have a concentration in the range of 0.02 to 0.12 wt % first mixed with the ultra-high molecular weight polyethylene and then molded with the ultra-high molecular weight polyethylene at a temperature greater than the melting point of the ultra-high molecular weight polyethylene. The ultra-high molecular weight polyethylene and vitamin E may be gamma irradiated with a dosage of radiation between 5 and 20 Mrad. The insert may be machined prior to gamma irradiating the insert such that the gamma irradiation, at suitably high dosages, may also sterilize the insert.

Materials and Methods

Gamma-sterilized UHMWPE was compression molded into sheets (GUR® 1020, Quadrant, Germany), machined, packaged in inert gas atmosphere and gamma sterilized with a dose of 3 Mrad. Vitamin E blended samples were produced by mixing UHMWPE resin powder with 0.03, 0.05 or 0.1 wt % α-tocopherol, compression molded into blocks, gamma-irradiated with 7 to 20 Mrad in air and machined into the desired shape. Some of the samples were additionally gamma-sterilized with a dose of 3 Mrad. No thermal post-irradiation treatment was applied.

The free radical content was determined immediately after irradiation by electron spin resonance (ESR, Bruker) on cylinders (length 15 mm, diameter 4 mm) cut from the center of the blocks. The number of free radicals was calculated by double integration of the ESR signal, normalizing by sample weight and calibrating with DPPH.

Oxidation indices (OI) were quantified by Fourier Transform Infrared Spectroscopy (FTIR) according to ASTM F2102-06. Oxidation profiles were recorded with 150 μm thick slices to a depth of 2.5 mm from the surface. Prior to the OI measurements, all samples were artificially aged in an oxygen bomb at 5 bar oxygen pressure and 70° C. for two weeks (ASTM F2003-02).

Crosslink density, represented by the molecular weight between crosslinks (Mc), was obtained by swelling experiments according to ASTM D 2765-95 Method C on 3 samples per material (10×10×10 mm).

Mechanical testing: Double-notched Charpy impact testing was performed according to DIN EN ISO 11542-2 (min. 4 specimens per material) and tensile testing according to ASTM D638 (min. 5 specimens per material) using a test speed of 50 mm/min.

Hip simulator testing against 28 mm ceramic balls was performed on an AMTI hip simulator reproducing the human gait cycle with a frequency of 1.2 Hz and newborn calf serum (30 g/l protein concentration) as lubricant. Gravimetric wear was determined by weighing the acetabular cups every 0.5 mio cycles and by correcting the obtained results with a soak control cup.

In view of the foregoing, it will be seen that the several advantages of the invention are achieved and attained.

The embodiments were chosen and described in order to best explain the principles of the invention and its practical application to thereby enable others skilled in the art to best utilize the invention in various embodiments and with various modifications as are suited to the particular use contemplated.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described exemplary embodiments, but should be defined only in accordance with the following claims appended hereto and their equivalents.

What is claimed is:

1. A method of preparing a composition, comprising:
providing an ultra-high molecular weight polyethylene;
providing vitamin E first mixed with the ultra-high molecular weight polyethylene such that the mix has a vitamin E concentration in the range of 0.02 to 0.12 wt % and then molded with the ultra-high molecular weight polyethylene at a temperature greater than the melting point of the ultra-high molecular weight polyethylene and thereby forming a molded composition; and
gamma irradiating the molded composition in air with a dosage of radiation between 5 and 20 Mrad, wherein the dosage of radiation is proportional to the concentration of vitamin E in the mix.

2. The method of claim 1, wherein the concentration of vitamin E is in the range of 0.03 to 0.1 wt %.

3. The method of claim 1, wherein the vitamin E is tocopherol.

4. The method of claim 1, wherein the vitamin E is alpha-tocopherol.

5. The method of claim 1, wherein the gamma irradiation is a dosage within the range of 7 to 15 Mrad.

6. The method of claim 1, wherein the gamma irradiation is a dosage within the range of 9 to 11 Mrad.

7. The method of claim 1, wherein the composition is further gamma sterilized with a dosage within the range of 2.5 to 4 Mrad.

8. The method of claim 1, wherein the composition is further gamma sterilized with a dosage of 3 Mrad.

9. The method of claim 1, wherein the molded composition undergoes no further thermal treatment.

10. The method of claim 8, wherein the composition is gamma sterilized in an inert gas.

11. The method of claim 1, wherein the ultra-high molecular weight polyethylene is a powder, the powder having a multimodal molecular weight distribution including a portion of the powder having a low molecular weight.

12. A method of preparing a composition, comprising the steps of:
a. mixing a vitamin E having a concentration in the range of 0.02 to 0.12 wt % with an ultra-high molecular weight polyethylene;
b. molding the ultra-high molecular weight polyethylene and vitamin E mixture at a temperature greater than the melting temperature of the ultra-high molecular weight polyethylene;
c. gamma irradiating in air the molded ultra-high molecular weight polyethylene and vitamin E mixture at a dosage between 5 and 20 Mrad, wherein the irradiating dosage is determined relative to the concentration of vitamin E in the mixture.

13. The method of claim 12, wherein the concentration of vitamin E is in the range of 0.03 to 0.1 wt %.

14. The method of claim 12, wherein the vitamin E is tocopherol.

15. The method of claim 12, wherein the vitamin E is alpha-tocopherol.

16. The method of claim 12, wherein the irradiating step comprises gamma irradiating the molded ultra-high molecular weight polyethylene and vitamin E mixture at a dosage between 7 and 15 Mrad.

17. The method of claim 12, wherein the irradiating step comprises gamma irradiating the molded ultra-high molecular weight polyethylene and vitamin E mixture at a dosage between 9 and 11 Mrad.

18. A method of preparing a composition, comprising the steps of:
   a. mixing a vitamin E having a concentration in the range of 0.02 to 0.12 wt % with an ultra-high molecular weight polyethylene;
   b. molding the ultra-high molecular weight polyethylene and vitamin E mixture at a temperature greater than the melting temperature of the ultra-high molecular weight polyethylene;
   c. gamma irradiating in air the molded ultra-high molecular weight polyethylene and vitamin E mixture at a dosage between 5 and 20 Mrad; and
   d. varying the concentration of vitamin E proportionally to the dosage of gamma irradiation.

19. The method of claim 12, further comprising the step of gamma sterilizing the gamma irradiated and molded ultra-high molecular weight polyethylene and vitamin E mixture with a dosage between 2.5 and 4 Mrad.

20. The method of claim 12, further comprising the step of gamma sterilizing the gamma irradiated and molded ultra-high molecular weight polyethylene and vitamin E mixture with a dosage of 3 Mrad.

21. The method of claim 12, wherein the molded composition undergoes no further thermal treatment.

22. The method of claim 12, further comprising the step of annealing the composition at a temperature less than the melting temperature of the ultra-high molecular weight polyethylene.

23. The method of claim 1, wherein the molded composition comprises an insert having a first surface configured to contact a first prosthetic component and a bearing surface configured to articulate against a second prosthetic component.

* * * * *